Figure 1:
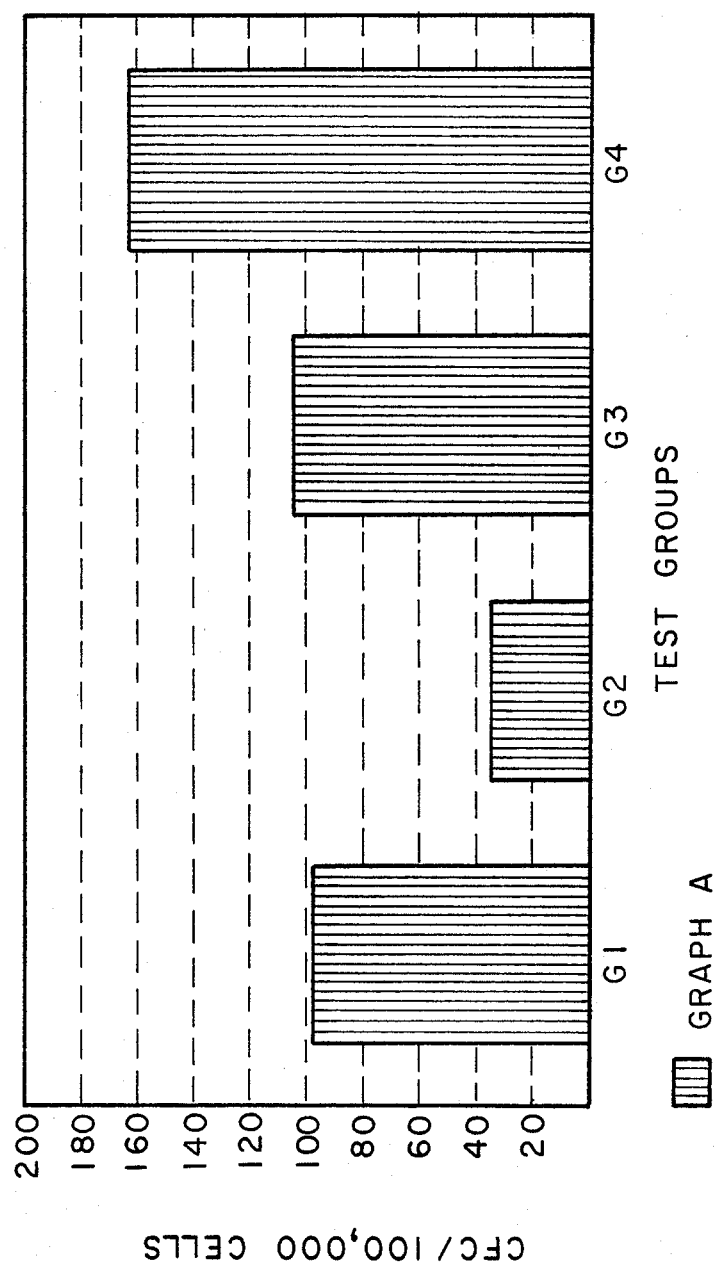

United States Patent [19]

Nair et al.

[11] Patent Number: 4,965,284

[45] Date of Patent: Oct. 23, 1990

[54] SUBSTITUTED DIBENZOTHIOPHENES

[75] Inventors: Vijay G. Nair, Nanuet; Ramson B. Conrow, Pearl River; Bosco S. Wang, Cranbury; V. M. Ruszala-Mallon, New City, all of N.Y.

[73] Assignee: American Cyanamid Company, Wayne, N.J.

[21] Appl. No.: 341,862

[22] Filed: Apr. 25, 1989

Related U.S. Application Data

[63] Continuation-in-part of Ser. No. 196,166, May 19, 1988, abandoned.

[51] Int. Cl.[5] ............................................ C07D 409/12
[52] U.S. Cl. ................................... 514/443; 564/225; 564/243; 564/244; 564/245; 549/46; 549/48; 549/59
[58] Field of Search ............... 564/245, 244, 243, 225; 549/48, 46, 59; 514/443

[56] References Cited

U.S. PATENT DOCUMENTS

| | | | |
|---|---|---|---|
| 2,149,335 | 3/1939 | Dahlen et al. ................. | 549/46 X |
| 2,563,795 | 8/1951 | Scalera et al. ................. | 549/46 OR |
| 3,083,201 | 3/1963 | Anderson ..................... | 549/46 X |
| 4,032,640 | 6/1977 | Bastian ........................ | 549/48 X |

FOREIGN PATENT DOCUMENTS

| | | | |
|---|---|---|---|
| 499134 | 1/1954 | Canada ......................... | 549/46 |
| 553479 | 2/1958 | Canada ......................... | 549/46 |

OTHER PUBLICATIONS

Drugs of the Future vol. 12, No. 5, 1987.
Cancer Immunol Immunother (1986) 22:8–14.
Cancer Research 48, 2135–2137 Apr. 15, 1988.
Hilgetag, "Preparative Organic Chemistry", 1972, John Wiley & Sons, p. 502–503.

*Primary Examiner*—John M. Ford
*Assistant Examiner*—Catherine Scalzo
*Attorney, Agent, or Firm*—Kenneth J. Dow

[57] ABSTRACT

This disclosure described novel derivatives of dibenzothiophene, dibenzothiophene sulfoxide, dibenzothiophene sulfone, thioxanthene, thioxanthene sulfoxide and thioxanthene sulfone which are active as modulators of the mammalian immune response system.

23 Claims, 2 Drawing Sheets

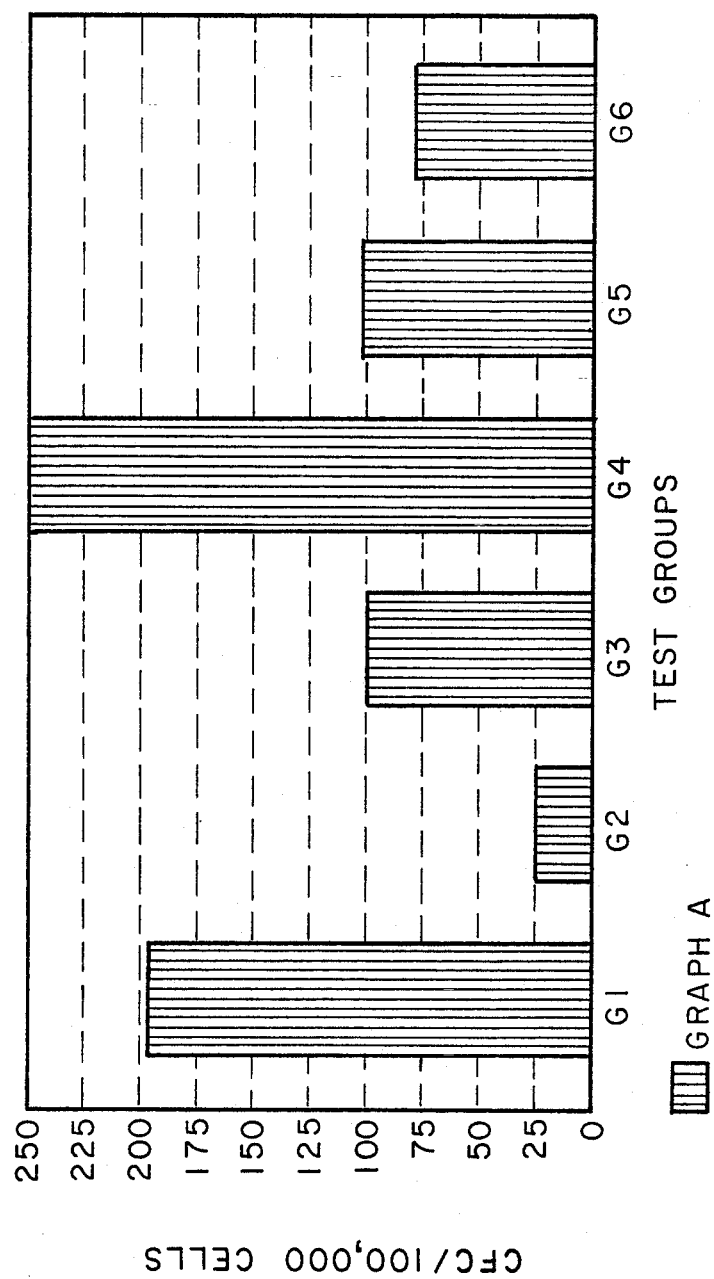

SUBSTITUTED DIBENZOTHIOPHENES

CROSS REFERENCE TO RELATED APPLICATION

This application is a continuation-in-part of our copending application Ser. No. 07/196,166, filed May 19, 1988 now abandoned.

BRIEF SUMMARY OF THE INVENTION

This invention relates to new organic compounds and, more particularly, is concerned with novel derivatives of dibenzothiophene, dibenzothiophene sulfoxide, dibenzothiophene sulfone, thioxanthene, thioxanthene sulfoxide and thioxanthene sulfone, which may be represented by the following structural formulae:

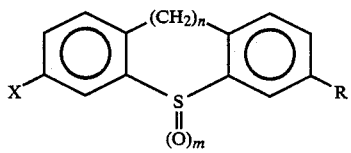
(I)

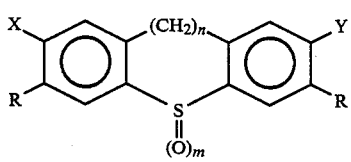
(II)

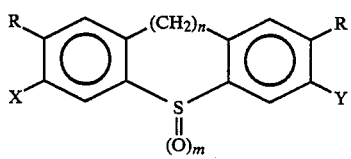
(III)

wherein
n is 0 or 1; m is 0, 1, or 2; X is hydrogen, fluoro, chloro or bromo; Y is hydrogen, fluoro, chloro or bromo; R is a moiety of the formulae:

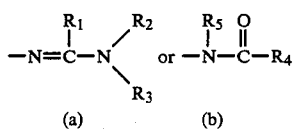

or R may also be —N=CHOC$_2$H$_5$, or

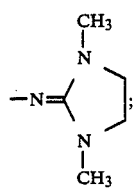

$R_1$ is hydrogen, alkyl or branched alkyl (C$_1$–C$_6$), phenyl, substituted phenyl, pyridine, thiophene or

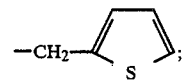

$R_2$ is hydrogen, alkyl or branched alkyl (C$_1$–C$_6$) or benzyl;

$R_3$ is alkyl or branched alkyl (C$_1$–C$_6$) or cycloalkyl (C$_3$–C$_6$);

$R_4$ is alkyl (C$_1$–C$_6$) or branched alkyl, phenyl, substituted phenyl,

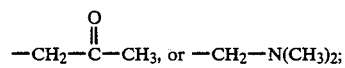

$R_5$ is hydrogen, alkyl or branched alkyl (C$_1$–C$_6$);

$R_1$ and $R_2$ taken together is —(CH$_2$)$_q$— wherein q is an integer from 2 to 5; and $R_2$ and $R_3$ taken together with the associated Nitrogen) is pyrrolidino, piperidino, morpholino, thiomorpholino, 4-methylpiperazino, 3-azabicyclo[3.2.2]nonyl, azetidino or azaspiro[5,5]undecanoyl.

The novel compounds of the present invention are obtainable as light yellow to orange crystalline materials having characteristic melting points and absorption spectra. The organic bases Ia, II and III of this invention form non-toxic acid-addition salts with a variety of pharmacologically acceptable organic and inorganic salt forming reagents. Thus, acid-addition salts, formed by admixture of the organic free base with one or two equivalents of an acid, suitably in a neutral solvent, are formed with such acids as sulfuric, phosphoric, hydrochloric, hydrobromic, sulfamic, citric, tartaric, acetic, gluconic, ascorbic, and the like. For purposes of this invention, the free bases are equivalent to their nontosic acid-addition salts.

The novel compounds of the present invention are active as modulators of the immune response system in mammals as demonstrated in experimental animals hereinafter. In addition, this invention is concerned with a method of modulating the immune response system in warm-blooded animals employing these compounds; with pharmaceutical compositions of matter containing them; and with chemical methods for their preparation.

DESCRIPTION OF THE INVENTION

The novel compounds I of the present invention may be readily prepared in accordance with the following reaction scheme:

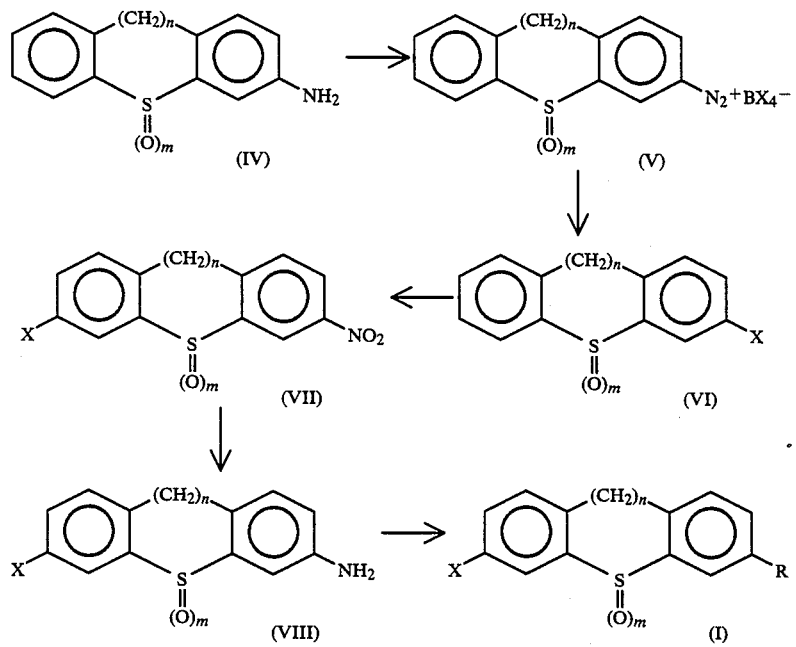

wherein n, m, X and R are as hereinabove defined. In accordance with the above reaction scheme, 3-aminodibenzothiophene sulfone (IV) is diazotized with sodium nitrite and hydrochloric acid in dimethylformamide at 5°-10° C., followed by reaction with the appropriate sodium tetrahaloborate to provide the corresponding diaoznium haloborate salt (V). Decomposition of V to provide VI is accomplished by heating in an inert atmosphere while the by-product boron trihalide gas is absorbed over a stirred solution of 5N sodium hydroxide. Nitration of VI to provide VII is achieved with 71% nitric acid in concentrated sulfuric acid at 18° C. Catalytic hydrogenation of VII with 5% palladium on carbon in a dioxane/glacial acetic acid solvent gives the corresponding 7-halo-3-dibenzothiopheneamine S,S-dioxide (VIII). Treatment of VIII with either a lower alkanoic acid anhydride

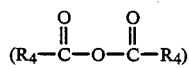

or a lower alkanoic acid chloride

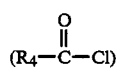

in pyridine at ambient temperature readily provides (Ib).

Also, the compounds Ia, IIa and IIIa may be readily prepared by first treating an appropriately substituted amide of the structural formula:

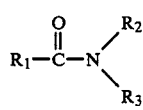

wherein $R_1$, $R_2$ and $R_3$ are as hereinbefore defined, with phosphorus oxychloride in dry acetonitrile at 0°-10° C., and then stirring until the temperature rises to room temperature. Then, either an equimolar amount of VIII or a hemimolar amount of 3,7-diaminodibenzothiophene (IX) or 2,8-diaminodibenzothiophene (X) is added to the reaction mixture and stirring is continued for a few hours at ambient temperature.

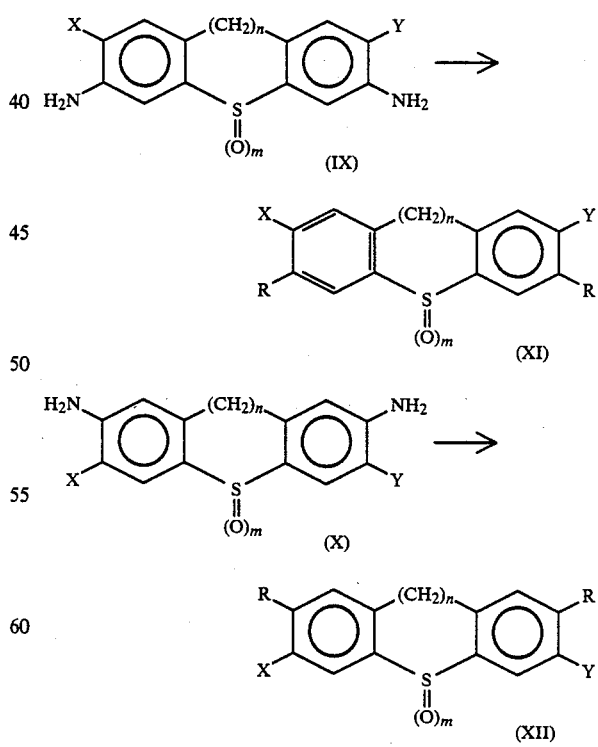

The reaction mixture is then poured into water and basified and the precipitated product is collected by filtration and recrystallized to give XI or XII.

The use of immunomodulators and chemotherapeutic adjuvants constitutes a new therapeutic approach to the treatment of immune deficiencies and cancer and is based on the concept that there are distinctive antigens in or on most tumor cells (embryonal or transplantation antigens), that distinguish them from normal host cells.

A majority of tumor immunologists favor the view that potentially malignant cells constantly arise but because of their "foreignness" they are normally eliminated by a competent humoral and cellular immune system. Occasionally however, tumor cells escape this immune surveillance and continue to reproduce and cancer results. The reason for the failure of the normally efficient immune surveillance mechanisms is not fully understood but it is thought that the immune system becomes less effective with increasing age. It is also depressed in certain genetic immuno-deficiency diseases, in various bacterial, fungal or viral infections, and in patients undergoing immuno-suppressive therapy. The growth of the neoplasm itself, as well as the various therapeutic modalities designed to treat the disease, e.g., cytotoxic chemotherapy and radiation, leads to a still greater depression of host resistance and results in an increased susceptibility to both exogenous and endogenous infections and perhaps accounts for the re-initiation of tumor growth and metastasis which frequently follows treatment-induced tumor remission.

This relationship between the immune system and tumor growth has been supported by experimental studies and observations in the clinical setting. Law, L. W., Nature, 205, 672-673 (1965) observed a marked increase in the incidence of polyoma tumors in thymectomized immunocompromised mice. In the clinical setting, Gatti, R. A. and Good, R. A., Cancer Genetics Lynch, H. T. (ed.) Charles Thomas, Springfield, Ill. (1976) observed that patients with immunodeficiencies appeared to have an increased susceptibility to neoplastic diseases and suggested that immune function had a relationship to malignancy. Eilber, F. R. and Morton, D. L., Cancer, 25, 362-367 (1970) also reported that cancer patients with an inability to develop a delayed type hypersensitivity response to skin test antigens generally had a poor prognosis. These observations that tumor initiation and progressive growth of malignant cells may be monitored and controlled by the host's immune network possibly via T cells, macrophages, or natural killer cells. On the other hand, the surveillance hypothesis has been questioned as a result of the apparent unrestricted growth of certain tumors in animals, Schwartz, R. S., New Engl. J. Med., 293. 181-184 (1975). The reasons for tumor cells escaping from surveillance are not completely understood, but several possibilities have been postulated including: (a) failure to recognize tumor antigens; (b) inability to mount adequate immune responses in order to destroy tumors; and (c) induction of immunodepression by oncogenic agents, blocking factors and/or suppressor cells. The ability to overcome these limitations via modulation of the immune defense system becomes important not only for the prophylaxis but also for the therapy of cancers.

If depression of the immune system can result in the growth of malignancies, regulation of any facet of the immune response may help the host to eliminate residual cancer cells. Therefore, it is desirable to search for chemical agents (i.e., immunomodulators) capable of restoring and stimulating host immune defense mechanisms in order to overcome the deficiencies which account for susceptibility to disease and failure to eradicate the cancer. Such immuno-modulating agents would likely be incapable of arresting the growth of a large tumor but their clinical utility would derive from their capacity to enhance normal immune surveillance mechanisms in patients whose tumor burden has been reduced by surgical, radiotherapeutic or chemotherapeutic methods.

Although a large number of agents including both biological and chemical substances have been tested for potential immunoenhancing activity against tumors, only a few have received critical evaluation in clinical trials [Oldham, R. K., J. Natl. Cancer Inst., 70, 789-796 (1986)]. Whether or not these candidates become therapeutically useful remains to be determined.

Nevertheless, experimental studies in animals have demonstrated the antitumor potential of a number of immunoregulants including live organisms of Bacillus Calmett-Guerin (BCG), Lamm, K. L., et al., Immunotherapy of Human Cancer, Terry and Rosenberg (eds.), 315-322, N.Y. (1982), *Corynebacterium parvum* (*C. parvum*), Bast, R. C., et al., Cancer Res., 42 1395-1401 (1983), thymosin, Dillman, R. O., et al., J. Biol. Resp. Modif., 1, 35-41 (1982), interferons, Louie, A., et al., Blood, 58, 717-718 (1981), monoclonal antibodies, Ritz, J. and Schlossman, S. F. Blood, 59, 1-11 (1982) interleukins, Lotze, M. T., et al., J. Biol. Resp. Modif., 3, 475-482 (1984), polynucleotides, and the anthelmintic drug, levamisole.

These substances have been shown to stimulate cellular immunity and to produce tumor regression. Some successes have been claimed in early clinical trials with BCG against malignant melanoma and acute leukemia, and with levamisole against lung cancer and breast cancer. Although the antitumor effects produced by these agents have been promising, significant therapeutic benefits have yet to be realized. Since this is a new therapeutic approach, new drugs and methods of treatment must receive careful clinical evaluation in order to reveal their full potential.

Modern research is directed to the discovery of a drug similar to but more potent than, known immunomodulators such as levamisole that would be effective in the eradication of tumor cells when used in conjunction with standard therapeutic measures. Stimulators of host resistance may be detected in animals models that can, in fact, detect both immunostimulators and anticancer agents. In one experimental animal model, mice are put in a condition simulating immunodepression common to cancer patients. This is accomplished by infecting mice with a leukemia virus which produces both leukemia and a disease-related immunodepression. Effective drugs are recognized by their ability to restore or enhance the antibody response in the experimental mice, or to inhibit tumor progression.

Such agents that would be capable of modulating the immune system would not only be useful in inhibiting tumor progression, but would be extremely useful as adjuncts in the chemotherapeutic or radiotherapeutic treatment of cancer and other related conditions. A major side effect associated with such chemotherapeutic or radiotherapeutic therapy is myelosuppression which then limits the dose of drug used and/or the frequency of treatment. Deaths due to chemo or irradiation associated myelosuppression are generally due to hemorrhage or sepsis. The hemorrhagic deaths are a result of thrombocytopenia, a drastic decrease in the number of platelets. Septic deaths are a result of neutropenia, a severe drop in neutrophils, the cell which plays a major role in recovery from bacterial infections. Septic deaths occur even when patients are treated with antibiotics.

However, it is known that with many cancers, the outcome may be better is one could use a more aggressive therapeutic approach by either increasing the dose or frequency of chemo or radiotherapy. Thus, a method for protecting the bone marrow from cytotoxic agents or accelerating the recovery of bone marrow cells following these regimens may allow for such aggressive therapy. One such approach to overcoming the hematologic toxicity associated with cancer therapies is autologous bone marrow transplantation to accelerate recovery of hematopoietic cells. More recently, several factors have been identified which are known stimulators of hematopoietic cell growth. These colony stimulating factors (CSFs) act on a variety of bone marrow progenitor cells to accelerate their differentiation into mature, active cell populations. Several of these factors have been cloned and are currently in trials in cancer patients who have undergone a variety of chemotherapeutic regimens. Results show that these agents, in particular, G-CSF (granulocyte colony stimulating factor) and GM-CSF (granulocyte-macrophage colony stimulating factor), could stimulate a sustained rise in neutrophil counts thus reducing the period of neutropenia after administration of a cytotoxic agent. A reduction in the number of days of neutropenia may prove beneficial not only in terms of hospital costs (by reducing the need for inpatient care) but ultimately in alleviating the morbidity and mortality associated with cancer therapy.

However, there are several drawbacks to treatment of chemotherapy associated myelosuppression with the recombinant colony stimulating factors. For one, there have been studies which indicate toxicities associated with GM-CSF therapy itself. Secondly, since the recombinant products are protein in nature, they have a relatively short half life when given intravenously. Thus, there is a need for continuous I.V. infusion to maintain therapeutically active levels. Thirdly, current studies are pointing to the need for combination therapy with various cytokines in order to obtain maximal responsiveness in bone marrow cell recovery. Compounds such as those described in this invention have several advantages over the recombinant CSFs. The primary advantage lies in the oral effectiveness of these immunomodulators, thus eliminating the need for continuous I.V. infusion and longer hospital stays. Secondly, the cost of manufacturing a synthetic compound is much less than that of a recombinant protein, thus translating into reduced cost for the patient. Thirdly, orally active synthetic compounds such as those described here are very stable compared with the recombinant proteins which are easily degraded once administered I.V. Thus, a single oral dose of the synthetic compounds results in therapeutic effects comparable to a 14 day continuous infusion regimen with the recombinant CSFs. And finally, one additional advantage of the synthetic compounds over the CSFs lies in the multiple cytokine induction by the synthetics, in particular, IL-1 and IL-2. Thus, one can achieve in a single oral dose with the synthetic compounds what multiple cytokines may do with repeated dosing.

The results as shown here suggest that these compounds may be an alternative to the CSFs to allow more aggressive therapy with cytotoxic drugs whose dose limiting toxicity is severe myelosuppression. Effective drugs in this series are recognized by their ability to accelerate recovery of bone marrow colony forming cells following 5-FU therapy and by stimulation of a colony forming activity in the serum of mice which allows for the proliferation of normal bone marrow cells in culture. Their radioprotective properties are measured by their ability to enhance the number of colony forming cells in the spleen of treated mice (endogenous CFU-S). Their ability to augment production of IL-1, a cytokine which acts synergistically with the CSFs, is measured by the ability of macrophage supernatants of treated mice to promote growth of IL-1 dependent cells in culture. Also, the ability of the compounds to augment production of IL-2, a cytokine which plays a major role in immunoregulation, is measured by the ability of supernatants obtained from Con-A stimulated splenocytes to promote growth of the CTLL-2 IL-2 dependent cell line.

In accordance with the present invention, the orally active compounds of this invention have been shown to be capable of modifying the reactivity of certain immune cell populations which may affect the growth of a tumor. Evidence of this effect on immune cell populations by the test compounds was seen with macrophages, which have long been recognized as an immune cell important in controlling the development and spread of neoplasms, Macknass, G. B., The Macrophage in Neoplasia, M. A. Fink (ed.), 3-13, Academic Press, N.Y. (1976). The test compounds apparently were able to activate these cells in vivo to inhibit the growth the tumor cells in cultures. These "activated" macrophages were detectable in peritoneal exudates of treated mice on day 4 after receiving a single oral dose of the test compound. (Table I). Macrophages and lymphocytes from treated mice release significantly more IL-1 and IL-2-like factors in culture than did the control counterparts. (Tables II and III). Sera from treated mice also possessed more colony stimulating factor than those from normal mice. (Table V). Mice treated with the test compounds also respond better to foreign antigens such as sheep red blood cells (SRBC) as shown by their ability to produce higher levels of antibody to this foreign protein. (Table IV). These experiments suggest that compounds of this invention may enhance the host's ability to respond to other foreign proteins such as those expressed on the surface of tumor cells.

The test compounds also accelerate recovery of bone marrow cells following chemotherapy in much the same way as the recombinant CSFs. (FIGS. 1-2).

The activity of the compounds of this invention as immunomodulators has been demonstrated in a series of procedures described below.

MATERIALS AND METHODS ANIMALS, TUMORS AND REAGENTS

C57BL/6 (B16, H-$2^b$), DBA/2 (D2, H-$2^d$), Balb/c (H-$2^d$), BDF1 (H-$2^d$) and CD2F1 (H-$2^d$) mice were obtained from Cumberland View Farms, Clinton, Tenn. C3H/HeJ (C3H, H-$2^k$) mice were obtained from the Jackson Laboratories, Bar Harbor, Me. All animals were used 6-10 weeks of age.

P815 mastocytoma was maintained in its syngeneic host. The appropriate tumor cells were used as targets in cytotoxicity assays. An interleukin-2 (IL-2) dependent cell line, designated CTLL-2, was maintained in culture in the presence of rat IL-2.

Hank's balanced salt solution (HBSS), RPMI 1640 medium, horse serum, fetal calf serum (FCS), L-glutamine, penicillin, streptomycin, Dulbecco's phosphate buffered saline (D-PSB), and N-2-hydroxyethyl-piperazine-N'-2-ethansulfonic acid (HEPES) were obtained from Grand Island Biological Company, Grand Island, N.Y. Gentamicin was obtained from Upjohn Co., Kalamazoo, Mich.; thioglycolate medium and lipopolysaccharide (LPS, *E. coli* 0128:B12) from DIFCO Laboratories, Detroit, Mich. $^{51}$Cr-sodium chromate ($^{51}$Cr, specific activity=300–500 Ci/g) and methyl-$^3$H-thymidine ($^3$HTdR, specific activity=20 Ci/mmol) were obtained from New England Nuclear, Boston, Mass.

I. ACTIVATION OF TUMORICIDAL MACROPHAGES

PREPARATION OF MURINE MACROPHAGES

Mice were injected intraperitoneally (IP) with 1 ml of thioglycolate medium and the peritoneal exudate (PE) cells were harvested 4–5 days later by washing their peritoneal cavities with HBSS containing 10 units/ml of heparin. PE cells were washed 3 times with HBSS and suspended in RPMI 1640 medium containing 10% FCS, 100 U/ml of penicillin, 100 μg/ml of gentamicin, 2 mM L-glutamine and 10 mM HEPES. The cells were dispensed into flat-bottom wells of 96-well culture plates (Costar, Cambridge, Mass.) and incubated at 37° C. for 2 hours. Non-adherent PE cells were removed by repeated and vigorous washings with HBSS and the majority of the remaining adherent cells (>95%) resembled macrophages morphologically and exhibited Mac-1 surface antigens as detected by fluorescence staining technique. These cells were also functionally active in ingesting latex particles.

ASSAY FOR MACROPHAGE MEDIATED TUMOR CYTOSTASIS

P815 tumor cells obtained from D2 mice were washed twice with HBSS and suspended in 10% FCS-complete medium. Five×$10^3$ P815 cells were added to culture wells containing B6 macrophages and the E:T ratios were determined by the numbers of PE cells added initially to each well. Unless otherwise noted, culture plates were incubated for 2 days. Target cells in each well were pulsed with 0.5 Ci $^2$HTdR for the final 4 hours and harvested by a cell harvester. The amount of $^3$HTdR incorporated into target cells was determined in a liquid scintillation counter. The mean cpm were obtained from triplicate cultures with results being presented as percent cytostasis calculated by the following formula: % cytostasis=(A−B)/A×100 were A=cpm of cultures containing normal control macrophages; and B=cpm of cultures containing experimental macrophages obtained from compound-treated mice.

TABLE I

| Activation of Tumoricidal Macrophages | |
|---|---|
| Compound | % Cytostasis |
| N-(7-Fluoro-3-dibenzothienyl)-acetamide S,S-dioxide | 13.9 |
| N-(7-Fluoro-3-dibenzothienyl)-N,N-dimethylpropaninidamide S,S-dioxide | 77.4 |

II. PRODUCTION OF IL-1

IL-1 ASSAY

Groups of C57B1/6 mice were treated orally with immunomodulator at doses of 25, 100 or 200 mg/Kg. Four days later peritoneal exudate cells (PEC) were collected and 1×$10^5$ cells were plated in RPMI-1640 medium containing 5% fetal calf serum (FCS). After 2 hours incubation at 37° C. the non-adherent cells were washed off and the adherent cells were incubated for 24 hours in RPMI medium with 5% FCS with or without Lipopolysaccharide (10 ug/ml). The following day the supernatants were collected and assayed for IL-1 on thymocytes. The cultures were incubated for 3 days and then pulsed with $^3$H-TdR using 0.5 μCi/well. The cells were harvested and the number of counts per minute (CPM) was determined using a Beckman scintillation counter.

TABLE II

| | IL-1 ASSAY | |
|---|---|---|
| Compound | − LPS | + LPS |
| Normals | 16,844 | 32,722 |
| N',N'''-3,7-Dibenzothiophene-diylbis[N,N-dimethylpropanimidamide] S,S-dioxide | 31,260 | 56,015 |
| N-(7-Fluoro-3-dibenzothienyl)-acetamide S,S-dioxide | 50,677 | 36,320 |
| N',N'''-2,8-Dibenzothiophene-diylbis[N,N-dimethylpropanimidamide] S,S-dioxide | 52,160 | 44,983 |

LPS = Lipopolysaccharide (10 μg/ml).

III. PRODUCTION OF IL-2

PREPARATION OF MOUSE LYMPHOCYTES

Spleens were removed from mice and single-cell suspensions were prepared by teasing the spleens apart and rinsing through No. 40 and No. 80 stainless steel mesh screens. Erythrocytes were lysed by a 3-minute exposure to a 0.83% Tris-ammonium chloride solution. Cells were washed 3 times with HBSS and finally suspended in complete RPMI 1640 culture medium consisting of 5% FCS, 2 mM L-glutamine, 5×$10^{-5}$ M 2-mercaptoethanol, 10 mM HEPES, 100 U/ml of penicillin, and 100 μg/ml of streptomycin. Cells were counted in a hemocytometer and the viability of test cells was always greater than 98% as judged by trypan blue dye exclusion.

PREPARATION OF VARIOUS SOLUBLE FACTORS AND THEIR ASSAYS

IL-2 was made by stimulating $10^7$ B6 splenocytes with 1 μg Con A in 1 ml medium. Supernatants were harvested 2 days later and residual Con A was removed by Sephadex G-50 absorption or α-methyl mannoside inactivation. IL-2 activity was tested in the thymocyte proliferation assay described above. Additionally, test samples were added to cultures of lymphoblasts prepared by a three-day Con A stimulation or to Il-2 dependent CTLL-2 cells. The proliferation of these indicator cells was measured 24 hours later by $^3$HTdR incorporation.

ENHANCEMENT AND RESTORATION OF THE PRODUCTION OF IL-2-LIKE FACTOR IN NORMAL MICE

Lymphocytes prepared from normal mice or mice treated with 100 mg/kg of test compound were stimulated with Con A for 2 days. Culture supernatants were harvested and tested for putative IL-2 activity in 3 proliferation assays using thymocytes, lymphoblasts and CTLL-2 cells as indicators. Although supernatants from normal lymphocytes supported the growth of all indicator cells, lymphocytes from treated animals apparently produced more IL-2 as indicated by a greater degree of cell proliferation in all three test systems.

TABLE III

IL-2 ASSAY

| Mouse Group | CPM % Supernatants Tested | | |
|---|---|---|---|
| | 20 | 10 | 5 |
| Normals | 6,548 | 4,230 | 2,093 |
| N',N'''-3,7-Dibenzothiophene-diylbis[N,N-dimethylpropanimidamide] S,S-dioxide | 14,568 | 9,050 | 3,238 |
| N-(7-Fluoro-3-dibenzothienyl)-acetamide S,S-dioxide | 10,982 | 5,653 | 2,849 |
| N',N'''-2,8-Dibenzothiophene-diylbis[N,N-dimethylpropanimidamide] S,S-dioxide | 11,288 | 6,457 | 2,766 |

IV. ANTI-SRBC ANTIBODY ASSAY

Compounds were given orally on day 0 at doses of 200 or 600 mg/kg. 0.1 ml of a 10% suspension of sheep RBC (Red Blood Cell) was given IP on day 4. Ten days later splenocytes were obtained from these mice and either $4 \times 10^6$ or $2 \times 10^6$ splenocytes in 50 µl were mixed with 50 µl of a 15% suspension of SRBC containing guinea pig complement (1:4 dilution). 100 µl of this mixture was placed onto a slide culture and incubated for 30 to 45 minutes at 37° C. The number of antibody forming cells was determined by counting the number of visible plaques formed.

TABLE IV

Production of Anti-SRBC Antibody

| Compound | CPM Test No. | |
|---|---|---|
| | 1 | 2 |
| N'N'''-3,7-Dibenzothiophene-diylbis[N,N-dimethylpropanimidamide] S,S-dioxide | 1,437 | NT |
| N-(7-Fluoro-3-dibenzothienyl)-acetamide S,S-dioxide | NT | 1,469 |
| N-(7-Fluoro-3-dibenzothienyl)-N,N-dimethylpropaninimidamide S,S-dioxide | NT | 1,474 |
| N'N'''-2,8-Dibenzothiophene-diylbis[N,N-dimethylpropanimidamide] S,S-dioxide | 1,029 | NT |
| Control | 1,260 | 830 |

NT = Not tested
Control = Untreated normal mice

V. COLONY STIMULATING FACTOR PRODUCTION

Preparation of Mouse Bone Marrow Cells

Mouse Femurs were removed and the marrow cells collected by aspiration through a 23 gauge needle and dispensed into 5 ml of RPMI 1640 culture medium. Aliquots were diluted with a 2% solution of acetic acid containing 0.2% crystal violet and the number of nucleated cells per femur was determined by direct count in a hemocytometer.

Effect on CSF Induction in Mice

Mouse sera were assayed for colony stimulating factor (CSF) in cultures of normal bone marrow cells. CSF was tested in a system in which $5 \times 10^4$ normal marrow cells were incubated with 10% test samples in each well of 96-well culture plates for 3 days. Proliferation of these cells was determined by $^3$HTdR incorporation.

TABLE IV

Production of Colony Stimulating Factor

| Compound | CPM Test No. | |
|---|---|---|
| | 1 | 2 |
| N'N'''-3,7-Dibenzothiophene-diylbis[N,N-dimethylpropanimidamide] S,S-dioxide | NT | 6,650 |
| N-(7-Fluoro-3-dibenzothienyl)-acetamide S,S-dioxide | 976 | NT |
| N-(7-Fluoro-3-dibenzothienyl)-N,N-dimethylpropaninimidamide S,S-dioxide | 1,353 | NT |
| N'N'''-2,8-Dibenzothiophene-diylbis[N,N-dimethylpropanimidamide] S,S-dioxide | NT | 6,513 |
| Control | 548 | 3,118 |

NT = Not tested
Control = Untreated normal mice

VI. CFU-C ASSAY TO MEASURE ACCELERATION OF MYELOID CELL RECOVERY FOLLOWING 5-FU THERAPY

Groups of C3H/Hej mice were treated I.P. with 5-Fluorouracil (5Fu) (150 mg/Kg). Four days later they were given one oral dose of immunomodulator at 25, 100, or 200 mg/Kg. Three days later the mice were sacrificed and bone marrow cells collected by aspiration through a 23 gauge needle and dispensed into 5 ml of RPMi-1640 culture medium. Aliquots were diluted with a 0.2% solution of acetic acid in PBS, containing 0.2% crystal violet. The number of nucleated cells per femur was determined by direct count in a hemocytometer. The cells were plated in agarose containing medium supplemented with an exogenous source of CSF (50 u/plate of GM-CSF). After 7 days in culture the number of colonies consisting of 50 or more cells are counted and the values expressed as CFU-C per 100,000 cells. The results are shown in FIGS. 1–2.

LEGEND FOR FIG. 1:

G1.=Normals
G2.=5-Fluorouracil
G3.=5Fluorouracil+control, N-[4-[(4-fluorophenyl)-sulfonyl[phenyl]acetamide, (disclosed in U.S. Pat. No. 4,532,349) at 100 mg/Kg.
G4.=5-Fluorouracil+N-(7-Fluoro-3-dibenzothienyl-)acetamide S,S-dioxide at 200 mg/Kg

LEGEND FOR FIG. 2:

G1=Normal
G2=5-Fluorouracil
G3=5-Fluorouracil+control, N-[4-[(4-Fluorophenyl)-sulfonyl]phenyl]acetamide (U.S. Pat. No. 4,532,349) at 100 mg/Kg.
G4=5-Fluorouracil+N,N'''-2,8-Dibenzothiophenediylbis[N,N-dimethylpropanimidamide]S,S-dioxide at 100 mg/Kg.
G5=5-Fluorouracil+N',N'''-3,7-Dibenothiophenediylbis[N,N-dimethylpropanimidamide]S,S-dioxide at 200 mg/Kg.

The compounds of the present invention are effective as immunomodulators (that is, they modulate the immune response) when administered in amounts ranging from about 5 mg to about 400 mg/kg of body weight per day. A preferred dosage regimen for optimum results would be from about 25 mg to about 500 mg/kg of body weight per day. This dosage regimen may be adjusted to provide the optimum therapeutic response. For example, several divided doses may be administered daily or the dose may be proportionally reduced as indicated by the exigencies of the therapeutic situation. A practical advantage of this invention is that the active compounds may be administered in any convenient manner such as the oral or buccal routes.

The compounds of the present invention may be orally administered, for example with an inert diluent or with an assimilable edible carrier, or they may be enclosed in hard or soft shell gelatin capsules, or they may be compressed into tablets. For oral therapeutic administration, the active compounds may be incorporated with excipients and used in the form of tablets, troches, capsules, elixirs, suspensions, syrups, wafers and the like. Such compositions and preparations should contain at least 0.5% of the active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 500 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-tosic in the amounts employed.

The invention will be described in greater detail in conjunction with the following specific examples.

EXAMPLE 1

3,7-Dinitrodibenzothiophene S,S-dioxide

To a solution of 43.25 g of dibenzothiophene sulfone and 400 ml of concentrated sulfuric acid, cooled in an ice bath, was added dropwise, over 15 minutes, 30.8 g (21 ml) of 90% nitric acid at 15°–20° C. The solution was stirred in the ice bath for 30 minutes, then poured over 2 liters of crushed ice. The solid was collected by filtration, washed with water until neutral and then dried at 100° C. The solid was dissolved in 270 ml of dimethylformamide at near reflux temperature, filtered through diatomaceous earth, rewarmed to near boiling and then diluted with 30 ml of water. The mixture was allowed to cool to room temperature and the resulting solid collected, washed with ethanol and ether then air dried giving 50.57 g of the desired product as a solid, mp 282°–287° C.

EXAMPLE 2

3,7-Diaminodibenzothiophene S,S-dioxide

A mixture of 10.0 g of 3,7-dinitrodibenzothiophene S,S-dioxide, 180 ml of dimethylformamide, 20 ml of glacial acetic acid and 1.0 g of 5% palladium on carbon was hydrogenated in a Parr apparatus until hydrogen uptake ceased. The mixture was then filtered through diatomaceous earth, the filtrate poured into 1 liter of ice water, the solid collected by filtration, washed with ethanol and ether and dried at 110° C., giving 7.86 g of the desired product as a solid mp 320°–330° C.(dec.).

EXAMPLE 3

N',N'''-3,7-Dibenzothiophenediylbis[N,N-dimethylpropanimidamide]S,S-dioxide

To a mixture of 4,55 g of dimethylpropionamide in 20 ml of dry acetonitrile was added dropwise, under argon, over 2 minutes, 5.75 g of phosphorus oxychloride in 10 ml of dry acetonitrile. This mixture was allowed to stand for 100 minutes and then added to a solution of 3.69 g, of 3,7-diaminodibenzothiophene S,S-dioxide in 520 ml of dry acetonitrile. This mixture was stirred for 4 hours and then filtered through diatomaceous earth. The filtrate was evaporated, the residue dissolved in 100 ml of water and made strongly basic by the dropwise addition of 35 ml of 5N sodium hydroxide, with stirring. The resulting solid was collected, washed thoroughly with water and dried. This solid was crystallized from 100 ml of dimethylformamide:water (60:40), washed with water and dried, giving 4.07 g of the desired product as an orange-brown powder, mp 120°–122° C.

EXAMPLE 4

3-Nitrodibenzothiophene S,S-dioxide

To a solution of 43.25 g of dibenzothiophene sulfone in 400 ml of concentrated sulfuric acid, cooled in an ice/salt bath, was added dropwise at 0° to 2° C., 17.0 g of 71% nitric acid over 16 minutes. This mixture was stirred at 0° to −10° C. for 30 minutes and then poured over 2 liters of crushed ice. The solid was collected, washed with water until neutral and dried. This solid was dissolved in 750 ml giving three successive crops of precipitate. These crops were combined, giving 44.14 g of the desired product as a solid, mp 260°–267° C.

EXAMPLE 5

3-Aminodibenzothiophene S,S-dioxide

A 10 g portion of 3-nitrodibenzothiophene S,S-dioxide in 180 ml of dimethylformamide and 20 ml of glacial acetic acid containing 1.0 g of 5% palladium on carbon was hydrogenated for 1.75 hours, then filtered through diatomaceous earth and the filtrate evaporated. The residue was dissolved in 250 ml of acetonitrile, filtered through diatomaceous earth and concentrated to 150 ml. The solid was collected, giving 6.95 g of the desired product mp 261°–264° C.

EXAMPLE 6

3-Aminodibenzothiophene S,S-dioxide diazonium fluoborate

A solution of 12.49 g of 3-aminodibenzothiophene S,S-dioxide in 70 ml of dimethylformamide was added with stirring to 140 ml of 4N hydrochloric acid. This mixture was cooled in an ice bath and a solution of 3.73 g of sodium nitrite in 25 ml of water was added dropwise at 5° to 10° C. over 15 minutes. This mixture was stirred in the ice bath for 30 minutes and then poured into 2.5 liters of cold (10° C.) water. This mixture was filtered and to the filtrate was added 55 ml of 3.67 M sodium tetrafluoborate. The solid was collected, washed with ethanol, ether and dried, giving 16.67 g of the desired product as a tan powder.

EXAMPLE 7

3-Fluorodibenzothiophene S,S-dioxide

The 16.67 g of diazonium fluoroborate salt was heated in an argon atmosphere, while the by-product boron trifluoride gas was absorbed over a stirred solution of 5N sodium hydroxide. The dark reaction solution solidified on cooling, then was dissolved in 200 ml of refluxing chloroform, treated with charcoal and filtered through hydrogen magnesium silicate. The filtrate was evaporated, the residue dissolved in 250 ml of refluxing ethyl acetate, concentrated to about 150 ml and allowed to crystallize. The first two crops were collected and combined, giving 9.83 g of the desired compound as tan crystals, mp 229°–233° C.

EXAMPLE 8

3-Fluoro-7-nitrodibenzothiophene S,S-dioxide

To a mixture of 8.94 g of 3-fluorodibenzothiophene S,S-dioxide in 100 ml of concentrated sulfuric acid, cooled at 18° C. in a water bath, was added dropwise 3.12 g of 71% nitric acid over 3 minutes. The mixture was stirred at room temperature for one hour, then poured over 500 ml of crushed ice and the solid collected, washed with water until neutral then dried at 100° C. This solid was dissolved in 200 ml of acetonitrile, treated with charcoal, filtered through diatomaceous earth and the filtrate concentrated to 110 ml producing successive crops of crystals. The first two crops were combined and recrystallized from 100 ml of acetonitrile, giving 7.56 g of the desired product as a solid, mp 275°–279° C.

EXAMPLE 9

7-Fluoro-3-dibenzothiopeneamine S,S-dioxide

A mixture of 4.2 g of 3-fluoro-7-nitrodibenzothiophene S,S-dioxide, 100 ml of dioxane, 25 ml of glacial acetic acid and 1.0 g of 5% palladium on carbon was hydrogenated for 30 minutes, then filtered through diatomaceous earth and evaporated. The residue was crystallized from 50 ml of acetonitrile, giving 2.85 g of the desired product as yellow crystals, mp 266°–270° C.

EXAMPLE 10

N-(7-Fluoro-3-dibenzothienyl)acetamide S,S-dioxide

A mixture of 1.25 of 7-fluoro-3-dibenzothiopheneamine S,S-dioxide and 15 ml of pyridine was warmed to 50° C. to produce a solution, then 3 ml of acetic anhydride was added. The solution was allowed to stand 1.5 hours, then poured into 100 ml of water and the solid collected, washed with water and dried. This solid was crystallized from 10 ml of dimethylformamide, giving 1.01 g of the desired product as orange crystals mp 348°–358° C.

EXAMPLE 11

N'-(7-Fluoro-3-dibenzothienyl(N,N-dimethyl-propanimidamide S,S-dioxide

To a solution of 759 mg of dimethylpropionamide in 5 ml of acetonitrile under argon, was added a solution of 958 mg of phosphorus oxychloride in 5 ml of acetonitrile. This mixture was allowed to stand for 80 minutes and was then added to a solution of 1.25 g of 7-fluoro-3-dibenzothiopheneamine S,S-dioxide in 160 ml of acetontrile. This mixture was stirred for 3 hours and then filtered. The filtrate was evaporated, the solid dissolved in 75 ml of hot water, then cooled and filtered. The filtrate was made basic to pH 11 with 5 ml of 5N sodium hydroxide. The precipitate was collected, washed with water until neutral, dissolved in 100 ml of boiling ethanol and concentrated to 20 ml. The concentrate was refrigerated and the solid collected, giving 782 mg of the desired product as pale yellow crystals, mp 190°–194° C.

EXAMPLE 12

2-Dibenzothienylmethyl ketone

To a solution of 147.4 g of dibenzothiophene in 1.6 liters of carbon tetrachloride, cooled in an ice bath, was added a filtered solution of 122.7 g of anhydrous aluminum chloride in 425 ml of dichloromethane and 65.4 ml of acetyl chloride at 10° C., over 45 minutes. The mixture was stirred for 20 minutes, then a mixture of 2.5 liters of crushed ice and 500 ml of concentrated hydrochloric acid was added in one portion. This mixture was stirred vigorously until the yellow color disappeared. The aqueous layer was separated and washed in 100 ml of carbon tetrachloride. The wash was combined with the organic layer, washed with two 2 liter portions of water, dried and evaporated. The residue was crystallized from 250 ml of toluene and 750 ml of ether, giving 85.9 g of the desired product as colorless crystals, mp 107°–110° C.

EXAMPLE 13

2,8-Diacetyldibenzothiophene

To a solution of 45.3 g of 2-dibenzothienyl methyl ketone in one liter of carbon disulfide was added 106 g of anhydrous aluminum chloride. To this was added 17.3 g of acetyl chloride over 8 minutes. This mixture was refluxed for 3 hours and then poured into a mixture of 2 liters of crushed ice and 400 ml of concentrated hydrochloride acid. This mixture was stirred until the green color had changed to pale tan, then the solid was collected washed with water and air dried. This solid was collected, washed with water and air dried. This solid was dissolved in 2 liters of hot acetontride, filtered, concentrated to about one liter and allowed to crystallize, giving 39.0 g of the desired product as tan crystals, mp 207°–210° C.

EXAMPLE 14

1,1'-(2,8-Dibenzothiophenediyl)bisethanone S,S-dioxide

To a solution of 39.0 g of 2,8-diacetyldibenzothiophene in 1.03 liters of dimethylformamide at 40° C., was added 78.4 g of 80% m-chloroperoxybenzoic acid. This mixture was stirred at room temperature for 2.5 hours, then warmed to 40° C., 31.35 g of m-chloroperoxybenzoic acid was added and the mixture stirred overnight at room temperature. The mixture was then warmed to 70° C. and stirred for 5 hours at room temperature. The reaction was then poured into a stirred mixture of 5 liters of water and 103 g of sodium carbonate and the solid collected, washed with water and dried. This solid was crystallized from 325 ml of dimethylformamide, giving 37.54 g of the desired product as beige crystals, mp 284°–287° C.

EXAMPLE 15

1,1'-(2,8-Dibenzothiophenediyl)bisethanone, dioxime S,S-dioxide

A mixture of 39.2 g of 1,1'-(2,8-dibenzothiophenediyl)bisethanone S,S-dioxide and 39.0 g of hydroxylamine hydrochloride in 390 ml of pyridine was refluxed for one hour, then concentrated in vacuo until it solidified. This solid was broken up, stirred with 750 ml of water, filtered, washed with water and air dried, giving 42.4 g of the desired product as a cream colored powder, mp 309°–310° C.(dec.).

EXAMPLE 16

N',N'''-2,8-Dibenzothiophenediylbisacetamide S,S-dioxide

To a boiling solution of 1.0 g of 1,1'-(2,8-dibenzothiophenediyl)bisethanone, dioxime, S,S-dioxide in 20 ml of tetrahydrofuran was added portionwise, 40 ml of toluene until all of the tetrahydrofuran had boiled off. To the remaining toluene suspension at about 75° C., was added 1.39 g of phosphorus pentachloride over about 30 seconds. The solution was stirred at 75°–80° C. for 10 minutes, then cooled to room temperature, poured over 50 ml of crushed ice and neutralized with a solution of 2.5 g of anhydrous sodium carbonate in 10 ml of water. A 10 ml portion of saturated sodium chloride solution was added, the mixture heated to near boiling, then cooled to room temperature and the solid collected, washed with water and air dried, giving 1.03 g of the desired product as a beige powder, mp 330°–335° C.

EXAMPLE 17

2,8-Dibenzothiophenediamine S,S-dioxide

A mixture of 750 mg of N',N'''-2,8-dibenzothiophenediylbisacetamide S,S-dioxide, 5 ml of concentrated hydrochloric acid and 5 ml of acetic acid was refluxed for 1.5 hours, then cooled and the solid collected, washed with acetonitrile and ether, giving 703 mg of the corresponding dihydrochloride as a colorless powder. A 695 mg portion of this powder was warmed with 15 ml of 50% aqueous ethanol, then 2.5 ml of 5N sodium hydroxide was added and the mixture was stirred at room temperature for 15 minutes. A 40 ml portion of water was added and the solid collected, washed with water and air dried, giving 495 mg of the desired product as off-white crystals, mp 322°–326° C.

EXAMPLE 18

N,N'''-2,8-Dibenzothiophenediylbis[N,N-dimethylpropanimidamide] S,S-dioxide

To a solution of 4.55 g of N,N-dimethylpropionamide in 20 ml of acetonitrile was added a solution of 5.75 g of phosphorus oxychloride in 10 ml of acetonitrile. The resulting solution was added to a solution of 3.69 g of 2,8-dibenzothiophenediamine S,S-dioxide in 500 ml of acetonitrile at about 75° C. The clear yellow solution was allowed to stand at room temperature for 4 hours, then was filtered through diatomaceous earth and evaporated. The residue was dissolved in 100 ml of water and made strongly basic (pH 12) with 35 ml of 5N sodium hydroxide. The solid was collected, washed with water until neutral and dried. This solid was dissolved in 50 ml of hot N,N-dimethylformamide, diluted with 25 ml of water and allowed to stand at room temperature. The cream colored crystals were collected, washed with ethanol and ether and dried, giving 5.3 g of the desired product, mp 237°–242° C.

EXAMPLE 19

N,N'-(2,8-Dibenzothiophenediyl) bisacetamide

This compound was prepared using 2,8-dibenzothiophenediamine and the conditions of Example 16 giving the desired product as a tan powder, mp 295°–298° C.

EXAMPLE 20

N,N''''-3,6-Thioxanthenediylbis[N,N-dimethylformamide] 10,10-dioxide, dihydrochloride A mixture of 10 g of 3,6-thioxanthenediamine 10,10-dioxide in excess N,N-dimethylformamide dimethyl acetal containing hydrochloric acid was refluxed for several hours. The volatiles were removed to a residue which was dried giving 9 g of the desired product as yellow powder, mp 344°–346°.

EXAMPLE 21

N,N'''-Thioxanthene-3,6-diylbis-N,N-diethylformamide

This product was obtained by using 3,6-thioxanthenediamine 10,10-dioxide and N,N-diethylacetamide following the procedure of Example 3, as a yellow powder, mp 110°–113° C.

EXAMPLE 22

N,N-Thioxanthene-3,6-diyldiformimidic diethyl ester

A solution of 3,6-dithioxanthenediamine 10,10-dioxide in excess triethylorthoformate was a catalytic amount of p-toluenesulfonic acid was heated at reflux for several hours. The volatiles were removed and the residue filtered and dried giving the desired product as a tan solid, mp 200°–205° C.

EXAMPLE 23

N',N'''-9H-Thioxanthene-3,6-diylbis-N,N-dimethylpropanimidamide 10,10-dioxide

The procedure of Example 26 was followed using 3,6-thioxanthenediamine 10,10-dioxide and N,N-dimethylpropionamide giving the desired product as a yellow powder.

EXAMPLE 24

N,N'''-9H-thioxanthene-3,6-diylbis-N,N-diethylpropanimidamide S,S-dioxide

The procedure of Example 26 was followed using 3,6-thioxanthenediamine 10,10-dioxide and N,N-diethylpropionamide giving the desired product as a yellow powder.

EXAMPLE 25

N',N'''-9H-Thioxanthene-3,6-diylbis-N,N-dimethylethanimidamide S,S-dioxide

A mixture of 2.1 g of N,N-dimethylacetamide and 2.2 ml of phosphorous oxychloride in 30 ml of acetonitrile was stirred at ambient temperature for 2 hours. While stirring 2.6 g of 3,6-thioxanthenediamine 10,10-dioxide was rapidly added followed by continuous stirring for 18 hours. The reaction mixture was filtered and the filtrate evaporated to a residue which was poured into ice water containing 5N sodium hydroxide. A yellow solid formed which was filtered and repeatedly washed with water then dried giving 3.5 g of the desired product as a yellow powder.

EXAMPLE 26

N,N'-9H-thioxanthene-3,6-diylbisacetamide 10,10-dioxide

A mixture of 2.6 g of 3,6-thioxanthenediamine 10,10-dioxide in 10 ml of pyridine containing 5 ml of acetic anhydride was stirred at ambient temperature for 18 hours. The mixture was poured into ice water and the solid collected, washed with water and dried giving 3.4 g of the desired product as a light grey powder.

EXAMPLE 27

N,N'-Bis(1-methyl-2-pyrrolidinylidene)-2,8-dibenzothiophenediamine 5,5-dioxide

To a solution of 595 mg of 1-methyl-2-pyrrolidinone in 3 ml of acetonitrile under inert gas was added a solution of 766.8 mg of phosphorous oxychloride in 1.5 ml of acetonitrile followed by stirring for 1.5 hours at ambient temperature. The resulting pale yellow solution was added to a solution of 2,8-dibenzothiophenediamine phenediamine S,S-dioxide in 70 ml of acetonitrile. The heat was removed and a solid began to separate then gradually dissolve. The solvent was removed and the residue dissolved in 50 ml of water followed by adjustment of the pH to 12 with 5N sodium hydroxide. Stirring was continued for 30 minutes and the precipitate filtered, then dried giving 830 mg of white solid. The product was crystallized from methylene chloride:-hexanes giving 552 mg of the desired compound as white crystals, mp 281°-283° C.

EXAMPLE 28

N,N'-Bis(1-methyl-2-pyrrolidinylidene)-3,7-dibenzothiophenediamine 5,5-dioxide

To a stirred solution of 595 mg of 1-methyl-2-pyrrolidinone in 3 ml of acetonitrile under inert gas was added a solution of 767 mg of phosphorous oxychloride in 1.5 ml of acetonitrile. Stirring was continued at ambient temperature for 1.5 hours. The resulting yellow solution was added to a solution of 436 mg of 3,7-diaminodibenzothiophene S,S-dioxide in 50 ml of acetonitrile. The heat was removed and the reaction mixture stirred at ambient temperature for 4 hours. The mixture was filtered through diatomaceous earth and the filtrate evaporated to a yellow oil which was dissolved in 50 ml of water. The pH was adjusted to 12 with 5N sodium hydroxide followed by stirring at ambient temperature for 36 hours. The filtered cake was washed with water, ethyl alcohol and ether. The cake was dissolved in ethyl alcohol followed by the addition of water. The resulting solid was filtered, washed with ethyl alcohol and dried giving 156 mg of the desired product as gold solid, mp 205°-208° C. The combined filtrates were extracted with methylene chloride. The organic layer was dried and evaporated to a residue which was dissolved in methylene chloride and diluted with hexanes giving 140 mg of the desired product after washing with ethyl alcohol and ether, then drying.

EXAMPLE 29

3-Acetyl-3-azaspiro[5.5]undecane

A solution of 7 ml of 3-azaspiro[5.5]undecane and 9.7 ml of acetic anhydride in 19.5 ml of tetrahydrofuran was refluxed for 3 hours. The volatiles were evaporated to a yellow oil which was distilled in a Kugelrohr still giving a yellow oil, BP 90°-100° C./200-atm. The distillate was purified by chromatography on silica gel using 1:1 ethyl acetate:hexanes giving 7.89 g of the desired product as a colorless oil.

EXAMPLE 30

4-Acetylthiomorpholine

The product of Example 30 was followed using thiomorpholine and acetic anhydride giving the desired product.

EXAMPLES 31-38

In the manner of Example 28 the following substituted 3,7-bidenzothiophenediamines of Table VI were prepared by reaction of the appropriate amide with 3,7-diaminodibenzothiophene.

TABLE VI

| Example | Amide | Product | mp |
|---|---|---|---|
| 31 | N,N-diethyl m-toluamide | N',N'''-3,7-Dibenzothiophenediyl-bis [N,N-diethyl-benzenecarboximidamide] S,S-dioxide | 185-188° C. |
| 32 | N,N-diethylacetamide | N',N'''-3,7-Dibenzothiophenediyl-bis [N,N-diethylethanimidamide] S,S-dioxide | 177-179° C. |
| 33 | N,N-n-butylacetamide | N',N'''-3,7-Dibenzothiophenediyl-bis [N,N-dibutylethanimidamide] S,S-dioxide | 142-143° C. |
| 34 | 1-cyclohexyl-2-pyrrolidinone | N,N'-Bis(1-cyclohexyl-2-pyrrolidinylidene) 3,7-bibenzothiophenediamine S,S-dioxide | 278-281° C. |
| 35 | 1-methylpiperidone | N,N'-Bis(1-methyl-2-piperidinylidene) 3,7-dibenzothiophenediamine S,S-dioxide | 196-198° C. |
| 36 | 3-acetyl-3-azaspirolo[5.5]undecane | 3,3'-[3,7-Dibenzothiophenediylbis(nitriloethylidnye)]bis-3-azaspiro-[5.5]undecane S,S-dioxide | 259-262° C. |
| 37 | N,N-diethyl-2-thiophenecarboxamide | N',N'''-3,7-Dibenzothiophenediylbis-[N,N-diethyl-2-thiophenecarboximidamide] $S^2,S^2$-dioxide | 225-228° C. |
| 38 | N-methylacetamide | N',N'''-3,7-Dibenzothiophenediylbis [N-methyl-ethanimid-amide] S,S-dioxide. | 155-160° C. |

EXAMPLE 39

1-Acetyl-azetidine

A 3.6 ml volume of acetic anhydride was added dropwise to a stirred solution of 2.0 g of Azetidine in 5 ml of tetrahydrofuran at 0° C. The cooling bath was removed and stirring continued for 18 hours. The solution was removed and the residue distilled in a Kugelrohr still followed by chromatography on silica gel using 2% methyl alcohol:methylene chloride to give 1.60 g of the desired product as an oil.

EXAMPLE 40

N-Butyl-3-methyl-N-(phenylmethyl)butaneamide

A stirred solution of 6.0 g of N-benzyl-n-butylamine in 3 ml of methylene chloride containing 4.5 ml of triethylamine, under inert gas, was cooled to 0° C. and treated by the dropwise addition of 4.27 ml of isovalerylchloride. Another 3 ml of methylene chloride was added and stirred at ambient temperature for 18 hours. The insolubles were filtered and the cake washed with methylene chloride. The combined filtrates were washed with water, brine and dried. Evaporation of the volatiles gave a brown oil which was purified by chromatography on silica gel using 1:8 ethyl acetate:-hexanes giving 7.75 g of the desired product as a yellowish oil.

EXAMPLE 41

3-Acetyl-3-azabicyclo]3.2.2]nonane

A solution of 5 g of 3-azabicyclo]3.2.2]-nonane and 75 g of acetic anhydride in 15 ml of tetrahydrofuran was refluxed for 3 hours. The solvent was removed and the oily residue crystallized from hot hexanes giving 4.78 g of the desired product as white crystals, mp 90°–93° C.

EXAMPLE 42

N,N-Diethylbenzamide

A stirred solution of 2.5 g of diethylamine and 3.5 g of triethylamine in 30 ml of methylene chloride was cooled in an ice bath while 4.9 g of benzoyl chloride was added dropwise. The cooling bath was removed and the mixture stirred at ambient temperature for 18 hours. The insolubles were removed by filtration followed by methylene chloride washing. The combined filtrates were washed with water and brine, dried and evaporated to a yellow oil which was distilled in a Kugelrohr still to give 5.91 g of the desired product as a colorless oil, 70°/300 mm.

EXAMPLE 43

N,N-Diethyl-2-thiopheneacetamide

The product of Example 42 was followed using 2-thiopheneacetyl chloride and diethylamine giving the desired product as an oil.

EXAMPLE 44

4-(Cyclobutylcarbonyl)thiomorpholine

The product of Example 42 was followed using thiomorpholine and cyclobutanecarbonyl chloride giving the desired product as a solid, mp 39°–40° C.

EXAMPLE 45

N,N-Diethyl-2-thiophenecarboxamide

The procedure of Example 42 was followed using 2-thiophenecarboxyl chloride and diethylamine giving the desired product as a solid, mp 50°–52° C.

EXAMPLE 46

4,4'-[2,8-Dibenzothiophenediylbis(nitriloethylidyne)]-bismorpholine S,S-dioxide A solution of 0.78 g of N-acetylmorpholine in 2.7 ml of acetonitrile was added to a stirred solution of 0.77 g of phosphorous oxychloride in 1.3 ml of acetonitrile. After one hour the resulting yellow solution was added to a stirred solution of 0.49 g of 2,8-dibenzothiophenediamine in 65 ml of acetonitrile. The mixture was stirred for 20 hours at ambient temperature then filtered. The filtrate was evaporated and the residue dissolved in water. The pH was adjusted to 13 with 5N sodium hydroxide and the resulting precipitate collected and washed with water. Crystallization from hot N,N-dimethylformamide gave 0.5 g of fluffy white solid, mp 320°–323° C.

EXAMPLES 47–53

In the manner of Example 46 the following substituted 2,8-dibenzothiophenes of Table VII were prepared by reaction of the appropriate amide with 2,8-dibenzothiophenediamine.

TABLE VII

| Example | Amide | Product | mp |
| --- | --- | --- | --- |
| 47 | 3-acetyl-3-azaspirolo-[5.5]undecane | 1,1'-[2,8-Dibenzothiophenediylbis-(nitriloethylidyne)]bisazetidine S,S-dioxide | 264–268° C. |
| 48 | N,N-diethyl-2-thiophenecarboxamide | 3,3'-[2,8-Dibenzothiophenediylbis-(nitriloethylidyne)]bis-3-azabicyclo-[3.2.2]nonane S,S-dioxide | 270–275° C. |
| 49 | 4-acetylthiomorpholine | N',N'''-2,8-Dibenzothiophenediylbis-[N-butyl-3-methyl-N-(phenylmethyl)-butanimidamide S,S-dioxide | oil |
| 50 | N-methylacetamide | N',N'''-2,8-Dibenzothiophenediylbis-[N,N,-diethylbenzenecarboximidamide] S,S-dioxide | 210–213° C. |
| 51 | 4-(cyclobutylcarbonyl)-thiomorpholine | 4,4'-[2,8-Dibenzothiophenediylbis-[nitrilo(cyclobutylmethylidyne)]]bis-thiomorpholine $S^4,S^4$-dioxide | |
| 52 | 1,3-dimethyl-2-imidazolidinone | N,N'-Bis(1,3-dimethyl-2-imidazolidinyl-idene-2,8-dibenzothiophenediamine S,S-dioxide | 235–240° C. |
| 53 | 4-acetylthiomorpholine | 4,4'-[2,8-Dibenzothiophenediylbis-(nitriloethylidyne)bisthiomorpholine S,S-dioxide | 284–287° C. |

EXAMPLE 54

N,N'-Dibenzothiophene-3,7-diyl)bis-]N-methylacetamide] S,S-dioxide

To a partial solution of 6.6 g of N,N'-9H-thioxanthene-3,6-diylbisacetamide 10,10-dioxide in 40-ml of N,N-dimethylformamide was added portionwise 1.7 g of sodium hydride. Stirring was continued for one hour followed by cooling to keep the internal temperature below 30° C. while a solution of 6.6 g of methyl iodide in 10 ml of N,N-dimethylformamide was added dropwise. Stirring was continued for 4 hours. The reaction was poured into water and the precipitate collected, washed with water and dried giving a solid which was crystallized with methyl alcohol:acetone giving 3.9 g of the desired product as colorless crystals, mp 280°–281° C.

EXAMPLE 55

3,7-Bis-acetacetamidodibenzothiophene 5,5-dioxide

To a stirred mixture of 97.6 g of ethyl acetoacetate and one g of diethanolamine in chlorobenzene at distillation temperature was added in portions 123 g of 3,7-diamino-dibenzothiophene S,S-dioxide. Distillation fractions were removed over a 40 minute period. The resulting slurry was filtered and the cake washed with ethyl alcohol, then dried giving 146 g of yellow solid. A 50 g sample was stirred with 3 l of 1N sodium hydroxide for 1.5 hours then filtered. The filtrate was acidified with hydrochloric acid and the insolubles filtered, washed with water and dried giving 21.0 g of the desired product as a yellow solid.

EXAMPLE 56

3,7-Bis(2-chloroacetamido)dibenzothiophene 5,5-dioxide

A slurry of 21.8 g of 3,7-diaminodibenzothiophene S,S-dioxide in 400 ml of acetone was cooled in an ice bath while 30.2 ml of chloroacetyl chloride was carefully added. The bath was removed and the mixture heated at 100° C. with stirring, then cooled and poured into ice water. The precipitate was collected, washed with water and dried giving 34.9 g of the desired product as a solid.

EXAMPLE 57

3,7-Bis(2-dimethylaminoacetamido)-dibenzothiophene 5,5-dioxide

A mixture of 18.6 of 3,7-bis(chloracetamido)-dibenzothiophene 5,5-dioxide and 108 g of 25% dimethylamine was refluxed for 2.5 hours, cooled, filtered and the cake washed well with water and then dried in a 100° C. oven. The cake was further heated at reflux with 108 g of 25% dimethylamine for 6 hours, cooled, filtered and the cake washed with water then dried to give 16.3 g of the desired product as a solid.

EXAMPLE 58

2,2'-(3,7-Dibenzothiophenediyldiimino)bis-]N,N,N-triethyl-2-oxo-ethanaminium]dichloride S,S-dioxide A stirred mixture of 3.7 g of 3,7-bis(chloroacetamindo)dibenzothiophene S,S-dioxide and 40 ml of triethylamine was refluxed for 72 hours. An additional 3.0 of 3,7-bis(chloroacetamimido)dibenzothiophene and 75 ml of N,N-dimethylformamide was added followed by heating at reflux for 1.5 hours. The mixture was cooled, filtered and the cake washed with ether. The cake was dried and crystallized from methyl alcohol:ether to give 6.5 g of the desired product as a solid, mp 230°–231° C.

EXAMPLE 59

N'-2-Dibenzothienyl-N,N-diethyl-2-thiopheneethanimidamide

The procedure of Example 28 was followed using 2-aminodibenzothiophene and N,N-diethyl-2-thiopheneacetamide giving the desired product as a solid, mp 114°–115° C. following purification on silica gel using methylene chloride.

EXAMPLE 60

N,N-(2,8-Dichlorodibenzothiophen-3,7-diyl)bisbenzamide S,S-dioxide

To a slurry of 6.3 g of N,N'-(2,8-dichlorodibenzothiophene-3,7-diyl)bisbenzamide S,S-dioxide in 61 ml of pyrridine was added to 7.0 g of benzoyl chloride over 15 minutes, followed by heating on a steam bath for one hour. The mixture was poured into water and the precipitate collected, washed with water and air dried to give 10.2 g of the desired compound as a solid, m.p.>400° C.

EXAMPLE 61

N,N'-(5,5-Dioxodibenzothiophene-3,7-diyl) bisbenzenamide

The procedure of Example 60 was followed using 3,7-diamino-dibenzothiophene S,S-dioxide and benzoyl chloride giving the desired product as a yellow solid.

EXAMPLE 62

N,N'''-2,6-Dibenzothiophenediylbis[N,N-dimethyl-propanimidamide] S,S-dioxide

To a solution of 4.55 g of N,N-dimethylpropionamide in 20 ml of acetonitrile was added a solution of 5.75 g of phosphorus oxychloride in 10 ml of acetonitrile. The resulting solution was added to a solution of 3.69 g of 2,6-dibenzothiophenediamine S,S-dioxide in 500 ml of acetonitrile at about 75° C. The clear yellow solution was allowed to stand at room temperature for 4 hours, then was filtered through diatomaceous earth and evaporated. The residue was dissolved in 100 ml of water and made strongly basic (pH 12) with 35 ml of 5N sodium hydroxide. The solid was collected, washed with water until neutral and dried. This solid was dissolved in 50 ml of hot N,N-dimethylformamide, diluted with 25 ml of water and allowed to stand at room temperature. The crystals were collected, washed with ethanol and ether and dried, giving 4.0 g of the desired product.

We claim:

1. A compound selected from the group consisting of those of the formulae:

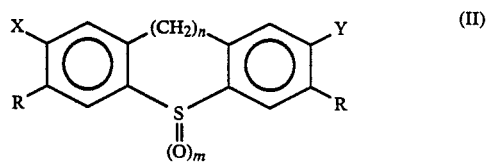
(II)

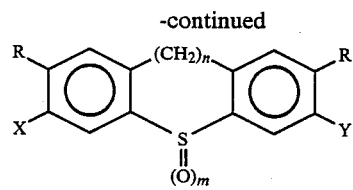

(III)

wherein
X is hydrogen, fluoro, chloro or bromo; Y is hydrogen, fluoro, chloro or bromo;
n is 0;
m is 1 or 2;
R is a moiety of the formula;

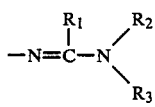

$R_1$ is alkyl or branched alkyl($C_1$–$C_6$), cycloalkyl ($C_3$–$C_6$), phenyl, methylphenyl, thiophene or

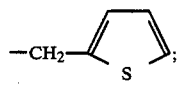

$R_2$ is hydrogen, alkyl or branched alkyl ($C_1$–$C_6$) or benzyl;

$R_3$ is alkyl or branched alkyl ($C_1$–$C_6$) or cycloalkyl ($C_3$–$C_6$) with the proviso that when X and Y are hydrogen and $R_1$ is phenyl or methylpehenyl, $R_2$ and $R_3$ cannot be hydrogen; and the pharmacologically acceptable acid-addition salts thereof.

2. The compound according to claim 1 of the formula II, wherein X and Y are hydrogen, $R_1$ is ethyl, and $R_2$ and $R_3$ are both methyl, m is 2 and n is 0; N′,N′′′-3,7-dibenzothiophenediylbis[N,N-dimethyl-propanimidamide] S,S-dioxide.

3. The compound according to claim 1 of the formula III, wherein X and Y are hydrogen, $R_1$ is ethyl, $R_2$ and $R_3$ are both methyl, m is 2 and n is 0; N′,N′′′-2,8-dibenzothiophenediylbis[N,N-dimethyl-propanimidamide] S,S-dioxide.

4. The compound according to claim 1 of the formula II, wherein X and Y are hydrogen, $R_1$ is methyl, $R_2$ and $R_3$ are ethyl, m is 2 and n is 0; N′,N′′′-3,7-dibenzothiophenediyl-bis[N,N-diethylethanimidamide] 5,5-dioxide.

5. The compound according to claim 1 of the formula II, where X and Y are hydrogen, $R_1$ is methyl, $R_2$ and $R_3$ are butyl, m is 2 and n is 0; N′,N′′′-3,7-dibenzothiophenediyl-bis(N,N-dibutylethanimidamide) 5,5-dioxide.

6. The compound according to claim 1 of the formula II, wherein X and Y are hydrogen, $R_1$ is 2-thiophene, m is 2, n is 0, and $R_2$ and $R_3$ are both ethyl; N′,N′′′-3,7-dibenzothiophenediyl-bis[N,N-diethyl-2-thiophene-carboximidamide] $S^2,S^2$-dioxide.

7. The compound according to claim 1 of the formula II, wherein X and Y are hydrogen, $R^1$ is methyl, $R^2$ is hydrogen, $R_3$ is methyl, m is 2 and n is 0; N,N′-3,7-dibenzothiophenediylbis-[N-methyl-ethanimidamide] S,S-dioxide.

8. The compound according to claim 1 of the formula III, wherein X and Y are hydrogen, $R_1$ is

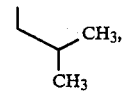

$R_2$ is benzyl, $R_3$ is n-butyl, m is 2 and n is 0; N′,N′′′-2,8-dibenzothiophenediylbis-[N-butyl-3-methyl-N-(phenylmethyl)-butanimidamide] S,S-dioxide.

9. The compound according to claim 1 of the formula III, wherein X and Y are hydrogen, $R_1$ is phenyl, $R_2$ and $R_3$ are ethyl, m is 2 and n is 0; N′,N′′′-2,8-dibenzothiophenediylbis[N,N-diethyl-benzenecarboximidamide] S,S-dioxide.

10. The compound according to claim 1 of the formula II, wherein X and Y are hydrogen, $R_1$ is 3-methylbenzene, $R_2$ and $R_3$ are both ethyl, m is 2 and n is 0; N,N-3,7-dibenzothiophenediylbis-[N,N-diethylbenzenecarboximidamide] S,S-dioxide.

11. The compound of the formula:

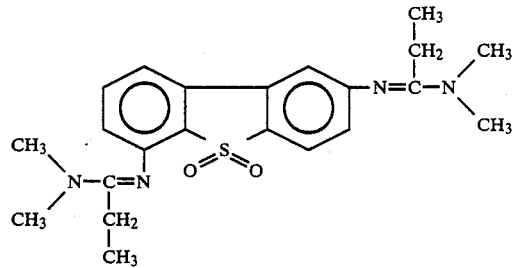

N,N′′′-2,6-dibenzothiophene diylbis [N,N-dimethyl-propanimidamide]S,S-dioxide.

12. A compound selected from the group consisting of those of the formulae:

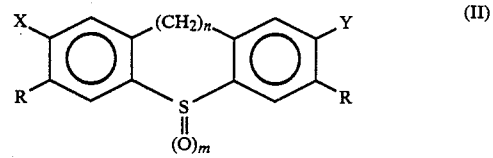

(II)

wherein
X and Y are hydrogen, fluoro, chloro or bromo;
n is 0;
m is 1 or 2;
R is a moiety of the formula:

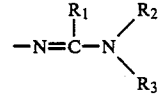

$R_1$ is alkyl or branched alkyl ($C_1$–$C_6$), cycloalkyl ($C_3$–$C_6$), phenyl, methylphenyl, thiophene or

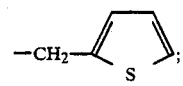

$R_2$ is hydrogen, alkyl or branched alkyl ($C_1$–$C_6$) or benzyl;

$R_3$ is alkyl or branched alkyl ($C_1$–$C_6$) or cycloalkyl ($C_3$–$C_6$) with the proviso that when X and Y are hydrogen and $R_1$ is phenyl or methylphenyl, $R_2$ and $R_3$ cannot be hydrogen; and the pharmacologically acceptable acid addition salts thereof.

13. A compound selected from the group consisting of those of the formula:

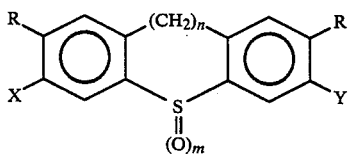

(III)

wherein
X and Y are hydrogen, fluoro, chloro or bromo,
n is 0;
m is 1 or 2;
R is a moiety of the formula:

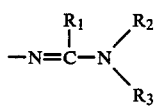

$R_1$ is alkyl or branched alkyl ($C_1$–$C_6$), phenyl, methylphenyl, thiophene or

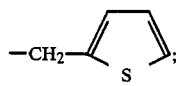

$R_2$ is hydrogen, alkyl or branched alkyl ($C_1$–$C_6$) or benzyl;
$R_3$ is alkyl or branched alkyl ($C_1$–$C_6$) or cycloalkyl ($C_3$–$C_6$) with the proviso that when X and Y are hydrogen and $R_1$ is phenyl or methylphenyl, $R_2$ and $R_3$ cannot be hydrogen; and the pharmacologically acceptable acid addition salts thereof.

14. A pharmaceutical composition comprising an immune response modulating amount of a compound according to claim 1 in association with a pharmaceutically acceptable carrier, diluent or excipient.

15. A composition according to claim 14 in unit dosage form.

16. A method of modulating the immune system in a warm-blood animal which comprises administering to said animal an immune response modulating amount of a compound according to claim 1.

17. A method of stimulating the proliferation and differentiation of blood cell progenitors in bone marrow of warm-blood animals which comprises administering to said animals a therapeutically effective amount of a compound according to claim 16.

18. A method of accelerating the recovery of white blood cell progenitors in bone marrow of warm blooded animals when used in conjunction with chemical or irradiation therapy which comprises administering to said animals a therapeutically effective amount of a compound according to claim 16.

19. A method of accelerating the recovery of white blood cell progenitors in bone marrow of warm blooded animals following chemical therapy which comprises administering to said animals a therapeutically effective amount of a compound according to claim 16.

20. A method of enhancing the activity of immune cells which inhibit tumor growth in warm blooded animals which comprises administering to said animals a therapeutically effective amount of a compound according to claim 16.

21. A method of enhancing the activity of immunoregulatory proteins which inhibit tumor growth in warm blooded animals which comprises administering to said animals a therapeutically effective amount of a compound according to claim 16.

22. A method of enhancing the activity of immune cells and immunoregulatory proteins which inhibit bacterial grown in warm blooded animals which comprises administering to said animals a therapeutically effective amount of a compound according to claim 16.

23. A method of enhancing the activity of immune cells and immunoregulatory proteins which inhibit viral grown in warm blooded animals which comprises administering to said animals a therapeutically effective amount of a compound according to claim 16.

* * * * *